United States Patent [19]

Schwoboda et al.

[11] 4,181,121

[45] Jan. 1, 1980

[54] SERIAL RELEASE MECHANISM AND DRAINAGE MONITOR EMBODYING THE SAME

[75] Inventors: George F. Schwoboda, New Brighton; Robert C. Wingrove, Afton, both of Minn.

[73] Assignee: Medical Devices, Inc., St. Paul, Minn.

[21] Appl. No.: 847,701

[22] Filed: Nov. 2, 1977

[51] Int. Cl.² .............................................. A61B 5/00
[52] U.S. Cl. ...................................... 128/762; 73/219; 74/3.52; 137/552.7; 137/624.19; 141/35; 251/7
[58] Field of Search ............... 128/2 F, 275, 276, 295, 128/DIG. 5; 74/3.52; 73/219, 422 R, 425.4 R; 137/552.7, 624.18, 624.19; 251/4, 7, 74; 141/35

[56] References Cited

U.S. PATENT DOCUMENTS

| | | | |
|---|---|---|---|
| 2,670,889 | 3/1954 | Heckendorf | 141/35 |
| 2,884,021 | 4/1959 | Ginsburg | 141/35 |
| 3,550,619 | 12/1970 | Halasz et al. | 251/7 X |
| 3,561,427 | 2/1971 | Profy | 128/2 F |
| 3,922,913 | 12/1975 | Scott | 73/219 |
| 4,077,395 | 3/1978 | Woolner | 128/2 F |

FOREIGN PATENT DOCUMENTS 2255878  7/1975  France .................................. 128/2 F 504183  4/1976  U.S.S.R. ..................................... 251/4

*Primary Examiner*—Richard T. Stouffer
*Attorney, Agent, or Firm*—Merchant, Gould, Smith, Edell, Welter & Schmidt

[57] ABSTRACT

A serial release mechanism, and a discharge monitor including the mechanism, which mechanism includes first and subsequent actuators slidable in a frame between working and withdrawn positions, springs urging the subsequent actuators into their working positions, latch tabs carried by the subsequent actuators and triggers resiliently pivoted to the frame for releasably retaining the subsequent actuators in their withdrawn positions, a shaft of noncircular cross section and a plurality of saddles for releasing the triggers of the subsequent actuators and having operating fingers and being rotatable with the shaft and slidable therealong between first positions in which they are aligned with the triggers and second positions in which they are not so aligned, saddle springs resiliently urging the saddles along the shaft into their second positions, and shifter springs carried by the actuators and the frame, and effective when any actuator is in working position to displace the succeeding saddle into its first position, so that subsequent rotation of the shaft causes the finger to release the trigger.

2 Claims, 12 Drawing Figures

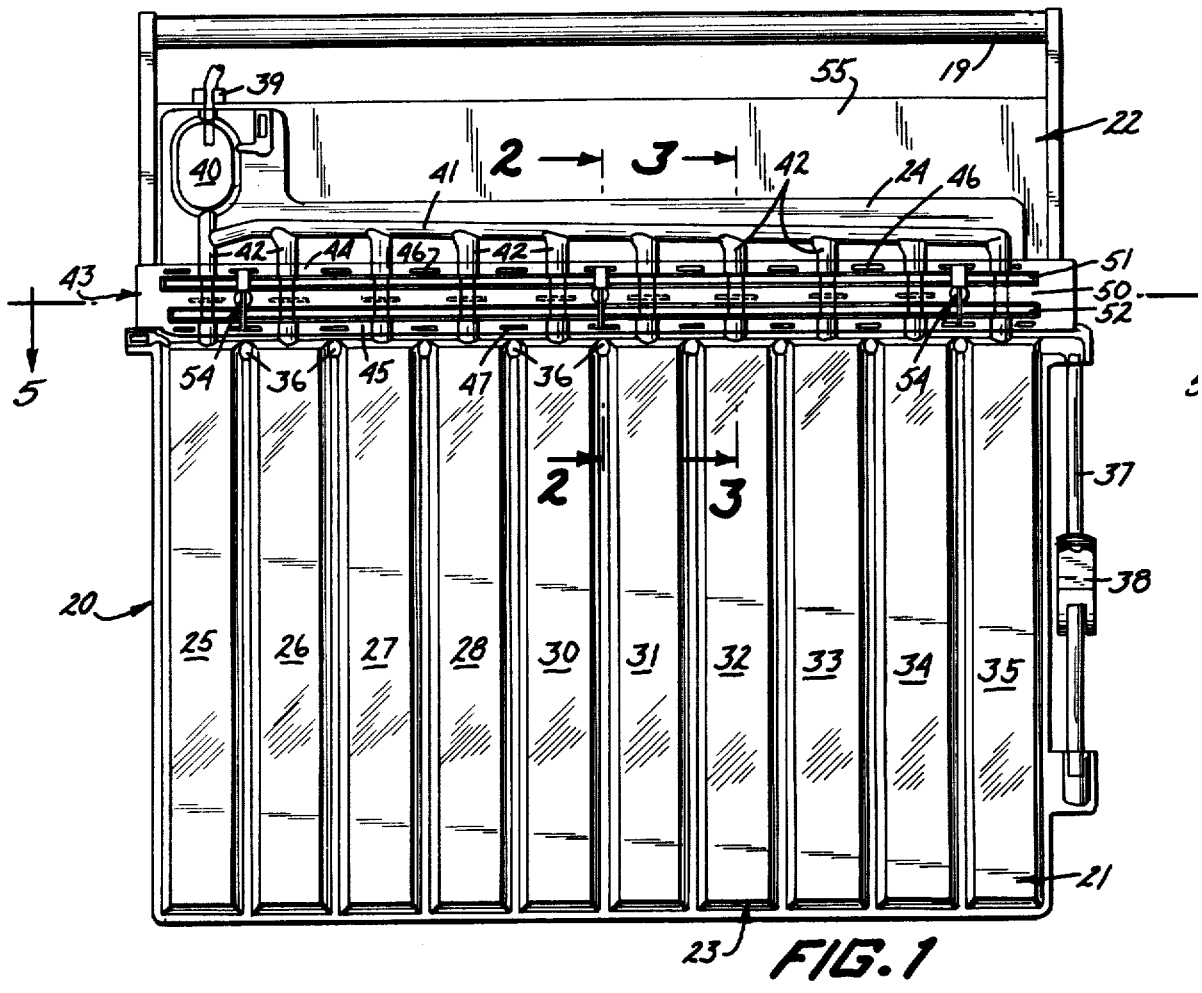
FIG. 1
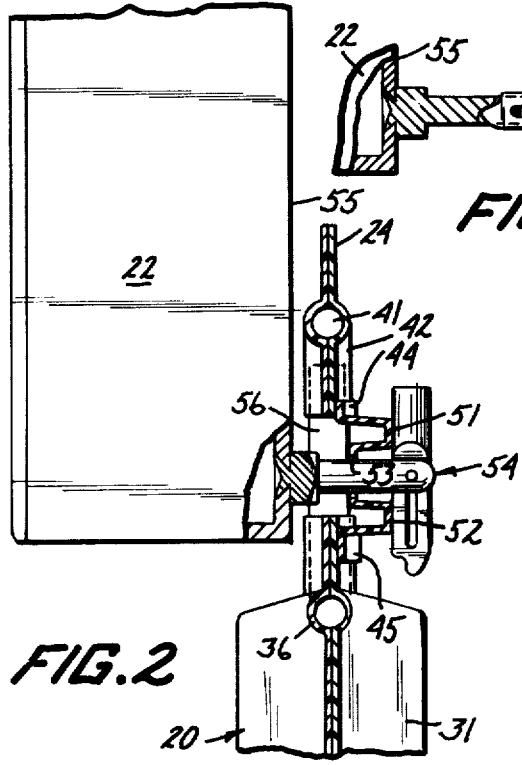
FIG. 2
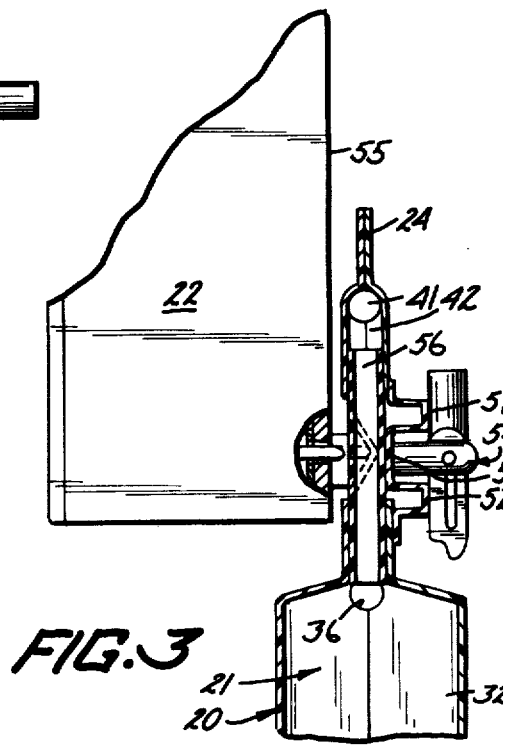
FIG. 3
FIG. 4

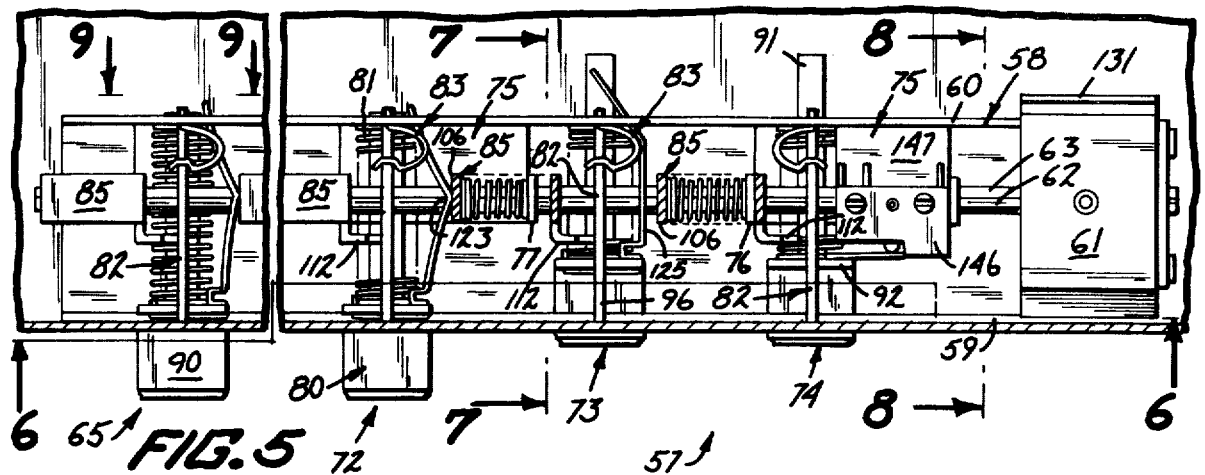
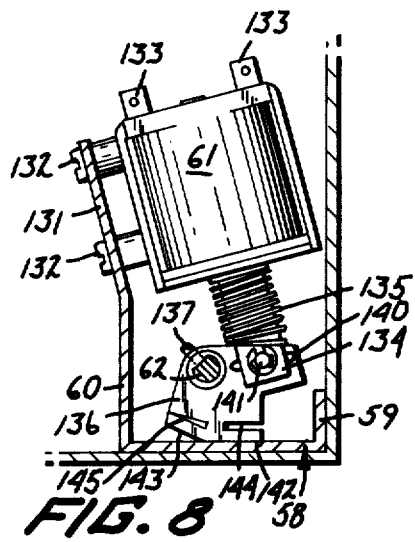
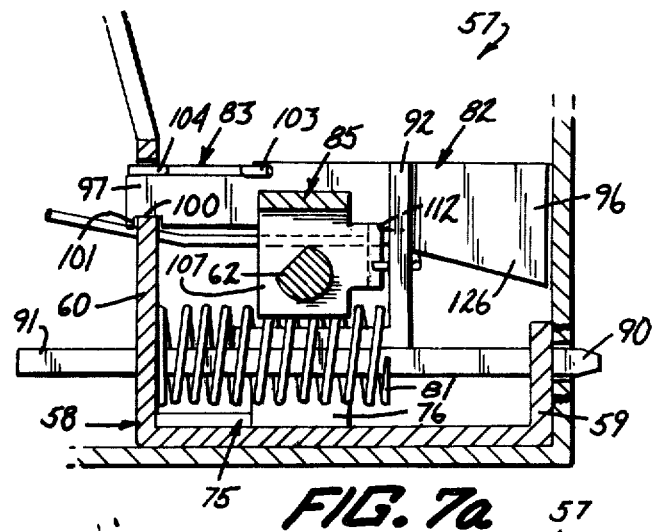
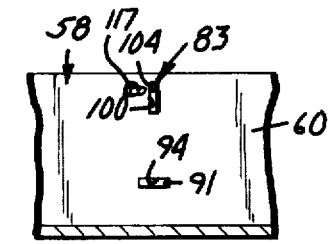
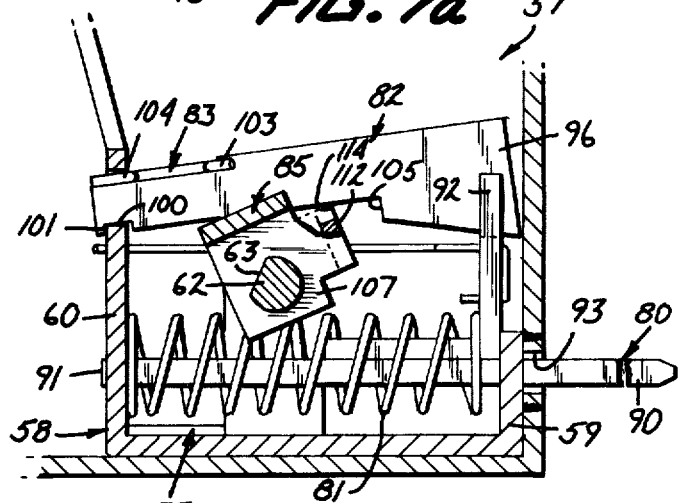
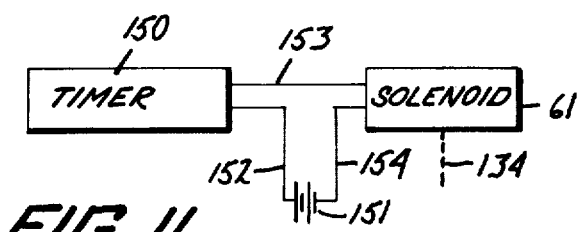

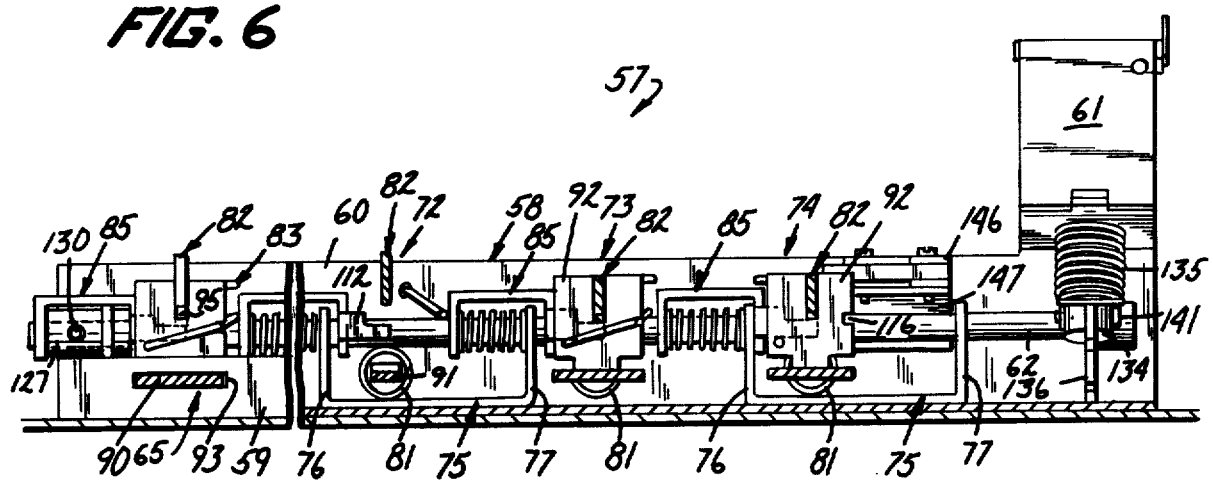
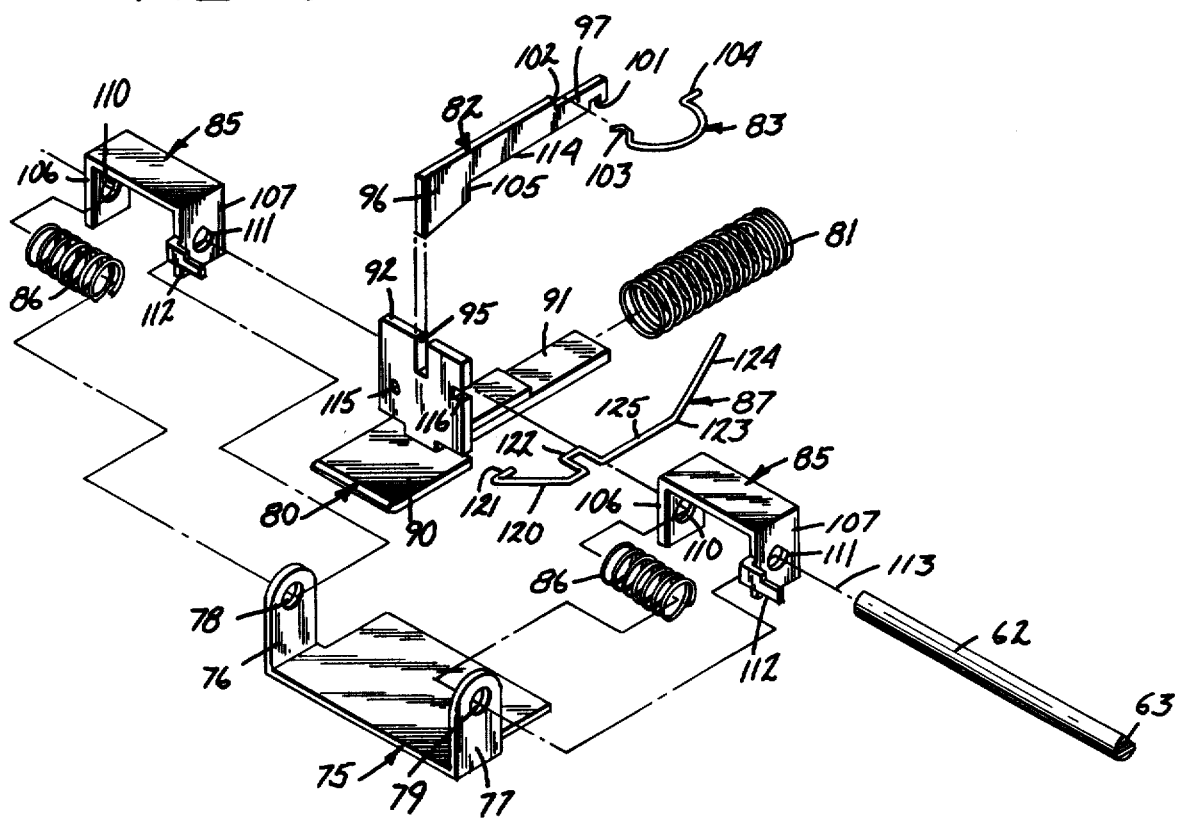

SERIAL RELEASE MECHANISM AND DRAINAGE MONITOR EMBODYING THE SAME

BACKGROUND OF THE INVENTION

This invention relates to the field of medicine, and particularly to apparatus whereby medical personnel may collect and keep reliable records of the liquid output of a patient. The equipment is specially designed for monitoring the volumetric urine output of a patient at regularly hourly intervals, for a total period longer than the usual work shift of hospital personnel.

The importance of knowledge of the patient's renal output is well known in medicine. A knowledge of the volumes of urine excreted by a patient over particular periods of time is extremely helpful in the management of fluid imbalances or electrolyte abnormalities. In cases where the patient has been in shock and the renal function is questionable, as in severe burn cases, urine output measurement is very important. Also, in virtually any serious illness, injury or operational procedure where a reduction in blood volume is anticipated, accurate measurement of small urinary volume output is either mandatory or highly desirable.

Accurate urine measurement are an aid in recognizing the onset of impending post-surgical shock. For this reason, the urine volumes of many post-surgical patients are measured hourly, particularly those who have undergone cardiac, thoracic, neurological or genitourinary surgery.

SUMMARY OF THE INVENTION

Numerous structures are known for monitoring the renal output of the patient, from a simple graduated cylinder at the end of an indwelling catheter to a highly mechanized arrangement such as that of Scott U.S. Pat. No. 3,194,069, for example. Our invention comprises an improvement on the structure shown in the copending patent application of one of us, Ser. No. 847,249, filed Oct. 31, 1977, and assigned to the assignee of the present application.

In the copending application there is disclosed a monitoring arrangement which has the advantages of completely unsupervised operation to collect, in sequential chambers, the excretions for ten successive hours, in a form resembling a bar graph or histogram for convenient observation in this closed or sealed system adapted either for emptying and resterilizing or preferably for disposable use, the manipulations at the end of the total collecting period to prepare for a second selection period are simple, convenient, and sanitary.

Our improvement, described and claimed herein, replaces the rather complex computer control of liquid flow of the earlier structure by a relatively simple serial release mechanism which eliminates the electronic counter, multivibrators, amplifiers, and multiple solenoids of the previous structure while performing the same functions. A timer energizes a single solenoid at predetermined intervals, and the diversion of liquid flow to the sequential chambers is all accomplished mechanically. This results in long periods of trouble free operation of the equipment, a special advantage in hospital use.

Various other advantages and features of novelty which characterize our invention are pointed out with particularity in the claims annexed hereto and forming a part hereof. However, for a better understanding of the invention, its advantages, and objects attained by its use, reference should be had to the drawing which forms a further part hereof, and to accompanying descriptive matter, in which there is illustrated and described a preferred embodiment of the invention.

BRIEF DESCRIPTION OF THE DRAWING

In the drawing, FIG. 1 is a view in elevation of a drainage monitor embodying our invention;

FIGS. 2 and 3 are fragmentary sectional views taken along the lines 2—2 and 3—3 of FIG. 1;

FIG. 4 shows a detail;

FIG. 5 is a plan view of our serial release mechanism, seen generally from the line 5—5 of FIG. 1, parts being shown in section;

FIG. 6 is a sectional view generally along the line 6—6 of FIG. 5;

FIGS. 7a and 7b are sectional views along the lines 7—7 in FIG. 5 showing different conditions of the apparatus;

FIG. 8 is a sectional view along the line 8—8 of FIG. 5;

FIG. 9 is a fragmentary rear view, seen from 9—9 of FIG. 5;

FIG. 10 is an exploded view of the elements of a subassembly used in the invention; and FIG. 11 is an electrical schematic.

DESCRIPTION OF THE PREFERRED EMBODIMENT

A drainage monitor 20 embodying our invention is shown in FIGS. 1-3 to comprise a liquid collector 21 and a control unit 22 having a handle 19. Collector 21 comprises a storage section 23 and a manifold section 24. Storage section 23 includes a row of chambers 25, 26, 27, 28, 30, 31, 32, 33, 34 and 35 into which liquid is to be delivered serially, beginning with chamber 25. The chambers are interconnected at their tops, as indicated at 36, and the interconnection is extended to an overflow connection 37 having a pinch clamp 38. Manifold section 24 includes an inlet 39, a drip chamber 40, and a header 41 having a plurality of taps 42 equal in number to the number of chambers. The sections are physically interconnected by a bridging member 43 having upper and lower flanges 44 and 45 sealed thereto as at 46 and 47, and including a central reaction bar 50 strengthened by longitudinal ribs 51 and 52 and formed with apertures 53 centrally and near its ends to pass toggle bolts 54 projecting outward from the front 55 of control unit 22. Liquid may pass from section 24 to section 23 through a plurality of collapsible flexible tubes 56 secured to taps 42 and the tops of chambers 25-35 inclusive. This arrangement is fully described in the copending application referred to above.

As shown in FIG. 3, flow of liquid from header 41 to each of the chambers, such as chamber 32, may be interrupted by means described more fully below, which compresses tube 56 against reaction bar 50, completely collapsing the tube so that no opening remains for passage of liquid therethrough. The normal state of tube 56 is shown in FIG. 3 in full lines, and its collapsed or occluded state in broken lines. Liquid from input 39 flows into chamber 25 until cut off, then into chamber 26, and so on. The serial release mechanism by which occlusion of tubes 56 in a desired order at predetermined times is accomplished will now be described.

As shown in FIGS. 5-10, serial release mechanism 57 comprises a frame 58 having a front wall 59 and a rear wall 60 and mounting a solenoid 61, which acts through a shaft 62 having a flat 63 to cause sequential operation of release sub-assemblies one less in number than the number of chambers 25-35: thus, sub-assembly 65 cooperates with the tube 56 leading to chamber 25, sub-assembly 72 with the tubes 56 leading to chamber 32, and so on. No sub-assembly is needed for the tube 56 leading to chamber 35, the final chamber in the series. The sub-assemblies are mounted on frame 58 and are suitably spaced in agreement with the spacing between the tubes 56 of a collector positioned on toggle bolts 54.

Shaft 62 is supported by a plurality of brackets 75 secured to frame 58 and having spaced left and right arms 76 and 77 with aligned apertures 78 and 79 to act as bearings for the shaft. In order to perform its function shaft 62 is noncircular, flat 63 extending its full length, but the depth of a flat is not enough to interfere with the bearing support offered by round apertures 78 and 79. The spacing between arms 76 and 77 of each bracket, and the spacings between the brackets, are such that each of sub-assemblies 65-74 is in operative coaction with an arm of a bracket.

As shown most clearly in the exploded view of FIG. 10, each sub-assembly comprises an actuator 80, an actuator spring 81, a trigger 82, a trigger spring 83, a release saddle 85, a saddle spring 86 (omitted in sub-assembly 65) and a shifter spring 87, all operationally interrelated as will now be described. Actuator 80 slides in frame 58 between working and withdrawn positions: it comprises a flat blade having a tongue 90 at one end and a tail 91 at the other end, and carries a latch tab 92. Frame 58 is provided with a plurality of front slots 93 to pass the tongues 90, and a plurality of rear slots 94 to pass the tails 91, of the actuators. Spring 81 functions to normally urge actuator 80 outward into its working position. To insert an actuator in the frame, a spring 81 is placed over tail 91 and the latter is positioned in line with the inside of a slot 94. The spring is compressed between tab 92 and rear wall 60, allowing tail 91 to move out through slot 94 until tongue 90 comes within the front wall 59 and can be aligned with slot 93: release of compression force allows spring 81 to move tongue 90 outwardly until tab 92 engages the inner surface of wall 59.

Trigger means are provided to releasably retain the actuators in the withdrawn positions. For this purpose latch tab 92 has a slot 95 sized to receive the front end 96 of trigger 82. The rear end 97 of trigger 82 passes through an aperture 100 in rear wall 60 and is upwardly notched at 101 to engage that wall: it is downwardly shouldered at 102 to engage end 103 of spring 83. The other end 104 of the spring is bent to engage the inner surface of wall 60, and then to pass through apertures 100, thus, securing the trigger in the opening. Springs 83 function to urge triggers 82 forwardly and downwardly, so that if pressure is applied inwardly to tongue 90, compressing spring 81, tab 92 slides rearwardly until it reaches a detent shoulder 105 formed in trigger 82, whereupon the trigger drops under the influence spring 83, holding actuator 80 out of its working position and in a withdrawn position.

Saddles 85 are provided to release triggers 82 and so allow actuators 80 to move from the withdrawn positions. Each saddle has legs 106 and 107 with aligned apertures 110 and 111 to receive shaft 62, one of them being noncircular so that the saddles rotate with the shaft, but may slide therealong. Leg 107 is formed with an operating finger 112 extending outwardly parallel to the axis 113 of shaft 62. As best indicated in FIG. 10, shaft 62 passes through aperture 111 of leg 107, then through arm 77 of bracket 75, then through spring 86, then through aperture 110 of leg 106, and so forth. By this arrangement spring 86 urges saddle 85 to the left on shaft 62 until the inner surface of leg 107 engages the outer surface of arm 77. In this position, as is shown in FIG. 7b, finger 112 does not extend under a central portion 114 of trigger 82, and clockwise rotation of shaft 62, while it rotates saddle 85 and finger 112 does not affect the trigger. Spring 86 thus disables the release function of the saddle 85 and shaft 62.

It is the function of shifter spring 87 to override the disabling function by displacing saddle 85 to the right, against the force of weaker spring 86, until finger 112 projects beneath trigger surface 114. Each tab 92 has an aperture 115 in its face and a notch 116 in its edge, and rear wall 60 has a plurality of apertures 117, for coaction with spring 87. One end 120 of the latter is formed with a 90° bend 121 received in apertures 115: it is held in slot 116 by a U-shaped bend 122, and is provided with a further bend 123 at an obtuse angle after which the other end 124 passes through apertures 117. As best shown in sub-assembly 73, FIG. 5, when actuator 90 is withdrawn, the portion 125 of spring 87 between bends 122 and 123 extends transversely across the frame, beside leg 106 of saddle 85 as displaced by spring 86, but not bearing significantly against it. Finger 112 is withdrawn from beneath trigger 82. However, when the actuator is in its working position, with tongue 90 extended, as in sub-assembly 72, the contact of end 124 of spring 87 with aperture 117 forces bend 123 of the spring to the right, against leg 106 of the saddle, compressing spring 86 and displacing the saddle so that the finger 112 contacts the face of trigger 82; when the shaft is released the finger passes beneath trigger 82. Rotation of shaft 62 may now lift the trigger until detent 105 clears the bottom of slot 95, and that spring 81 may move actuator 80 into its working position. Surface 126 of trigger 82 now rides on the bottom of slot 95, holding surface 114 above finger 112 to remove any load on finger 112 from spring 83 in this sub-assembly.

Referring to FIGS. 5 and 6, saddle 85 of sub-assembly 64 is not provided with a spring 86, but is secured against axial movement on shaft 62 by a collar 127 and set screw 130.

Turning now to FIG. 8, solenoid 61 is mounted on an extension 131 of rear wall 60 by suitable fasteners 132: the electrical terminals of the solenoid are showed at 133, and its plunger 134 is urged outwardly by spring 135. An actuating arm 136 is secured to shaft 62 by a set screw 137, and is slotted at 140 to receive a pin 141 at the end of plunger 134. Arm 136 is formed with projecting stop surfaces 142 and 143 to limit the movement of shaft 62 in each direction, slide adjustment being made possible by the provision of slots 144, 145.

A signalling miniature switch 146 may be mounted on a suitable bracket 147 for actuation by tab 92 of sub-assembly 74, if desired.

FIG. 11 shows the extremely simply electrical circuitry needed for this serial release mechanism. A timer 150 of any suitable electrical or mechanical type supplies brief electrical signals at predetermined intervals from any suitable source, here shown as a battery 151, to solenoid 61, on conductors 152, 153 and 154: each signal causes energization of the solenoid, and results in operation of the mechanism as will now be described.

OPERATION

The operation of a drainage monitor embodying our improved serial release mechanism will now be readily understood. A control unit having an adequate source of electrical energy is carried to the site of use and secured to a suitable support. Actuators 80 are displaced inwardly by manual pressure on tongues 90 until tabs 92 pass behind detents 105 of triggers 82, and the triggers drop, under the impulses of springs 83, to retain the actuators in withdrawn positions. Toggle bolts 54 are moved to their FIG. 4 positions, and a collector 21 is positioned so that apertures 53 in bar 50 pass over the toggle bolts, which are then moved to their FIG. 3 positions to maintain the collector in place. In this state of the equipment each tube 56 is in line with an actuator tongue 90, and its side away from the actuator is close to or in contact with bar 50. The discharge end of an indwelling catheter or other liquid source is connected to inlet 39, and operation of timer 150 is initiated. Liquid discharge drops through chamber 40, the first tap 42, and the first tube 56 into the first, left hand chamber 25 of storage section 23, where its quantity, color, and so forth can be visually observed.

At the end of one hour timer 150 supplies a short pulse to solenoid 61, which rotates shaft 62 and saddles 85 in a counterclockwise direction as seen in FIG. 8. Finger 112 of the first saddle is always beneath trigger 82, but the fingers of all the other saddles are displaced by their springs 86 to clear the respective triggers, as shown in FIG. 5 with respect to sub-assembly 74. Rotation of shaft 62 thus acts through saddle 85 and finger 112 of sub-assembly 65 only, to raise the trigger and release the actuator, the tongue 90 of which presses tube 56 against bar 50 so strongly as to close the tube. No more liquid may pass into chamber 25, but liquid continues to drop until the header tap at chamber 25 is filled, and then flows along header 24 to the next tap, in series, and so into chamber 26.

When the energization of solenoid 61 ceases, its plunger is withdrawn, and shaft 62 is returned to its initial position, by springs 135. Front portion 126 of trigger 82 now rests on the bottom of slot 95, and surface 114 of the trigger remains above the highest position of finger 112, although the latter remains beneath the trigger. Succeeding operations of solenoid 61 are thus ineffective against the trigger of any sub-assembly for which the actuator is in working position.

Movement of actuator 80 of sub-assembly 65 has moved spring 87 in aperture 117 so that bend 123 presses against leg 106 of the saddle 85 for the next sub-assembly, displacing saddle 85 by overcoming the force of spring 86 so that its finger 112 moves beneath its trigger. This is as shown in FIG. 5 for sub-assemblies 72 and 73. The next energization of solenoid 61 is to release the actuator of the sub-assembly next to sub-assembly 65, and so on.

Attention should now be directed to the relation between sub-assembly 72, 73 and 74, which clearly illustrate how the serial release of the actuators take place. Finger 112 in sub-assembly 74 is displaced to the left from beneath trigger 82, by spring 86. Finger 112 in sub-assembly 72 is beneath trigger 82, but the latter has released actuator 80 and is raised by slot 95 out of reach of finger 112. Bend 123 of spring 87 is in engagement with leg 106 of saddle 85, overcoming the force of spring 86 and displacing the saddle, and with it finger 112, to the right so that the finger is beneath trigger 82.

The next operation of shaft 62 will therefore be ineffective in sub-assembly 72, and all previous sub-assemblies in the series, and will be ineffective in sub-assembly 74, but will raise trigger 82 of sub-assembly 73, to release its actuator. FIG. 7a shows sub-assembly 73 with its actuator withdrawn, and FIG. 7b shows the same sub-assembly just after finger 112 has released trigger 82, which has been raised, by contact with the bottom of the slot in tab 92, out of engagement with finger 112 even while saddle 85 still remains rotated.

The foregoing explanation makes it clear that the mechanism operates upon each solenoid operation to release one actuator, the next in the series, whereby to cut off the flow of liquids to the successive chambers in turn. For other applications of the mechanism, it may be desired to release more than one actuator at a time. To release the actuators in threes, for example, it is only necessary to refrain from pressing in the actuator tongues for the first, fourth, and seventh sub-assemblies. These actuators only will then be in working positions initially, the fingers of the second, fifth and eighth sub-assemblies will be positioned beneath their respective triggers, and those in the third, sixth, and ninth sub-assemblies will not be so positioned. The next solenoid energization will accordingly release the triggers of the second, fifth and eighth actuators simultaneously, and so on. The same result may be even more neatly accomplished by substituting axially fixed saddles, such as that shown for sub-assembly 65, at the fourth and seventh sub-assemblies as well: by this expedient all nine of the sub-assemblies may have two positions.

Of course, a greater or lesser number of actuators may be used, by lengthening or shortening shaft 62, as the needs of particular special applications may dictate, and may be arranged for dual or multiple simultaneous operations rather than single operation, as may be desired.

From the foregoing it will be evident that we have invented a new and improved serial release mechanism and an improved discharge monitor in which the mechanism is particularly useful, although it will be of general utility wherever serial operation of single actuators or actuatores in pairs or sets is desired.

Numerous characteristics and advantages of our invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

What is claimed is:

1. A discharge monitor comprising, in combination:
   (1) a liquid collector including a series of storage chambers, a header for supplying liquid to said chambers, and collapsible tubes connecting said chambers to said header; and
   (2) a control unit for serially causing collapse of said tubes to cut off passage for liquid to said chambers, said control unit including
      (a) a series of actuators normally urged resiliently into first, working positions;
      (b) trigger means releasably holding said actuators in second, withdrawn positions;
      (c) trigger release means effective in a first state, when operated, to release said trigger means;

(d) means for operating said trigger release means;

(e) disabling means normally effective to actuate said trigger release means into a second state in which release of said trigger means thereby is prevented; and (f) override means effective, when any actuator in a series is in working position, to override the release disablement of only the next actuator in the series, so that successive operation of the operating means causes successive release of said actuators singly in series.

2. A discharge monitor comprising, in combination:

means supplying a liquid to be distributed; first and second storage chambers for receiving said liquid;

first and second collapsible elastic tubes for conducting said liquid to said chambers;

first and second actuators slidable in a frame between withdrawn positions and working positions in which they collapse said tubes to prevent liquid from flowing therethrough;

resilient means urging said second actuator into said working position;

trigger means, including a latch tab carried by said second actuator and a trigger resiliently pivoted to said frame, for releasably retaining said second actuator in said withdrawn position;

trigger release means including a shaft of noncircular cross section and a saddle having an operating finger, said saddle being rotatable with said shaft and slidable therealong between a first position, in which said finger is aligned with said trigger, and a second position, in which said finger is not aligned with said trigger;

disabling means, including a saddle spring, resiliently urging said saddle along said shaft into said second position, so that rotation of said shaft does not cause release of said trigger;

means for displacing said first actuator into its working position to prevent liquid flow to said first chamber;

and override means including a shifter spring carried by said first actuator and said frame, and effective when said first actuator is in working position to displace said saddle into said first position, so that subsequent rotation of said shaft causes said finger to release said trigger, to prevent liquid flow to said second chamber.

* * * * *